United States Patent
Cao et al.

(10) Patent No.: US 10,400,209 B2
(45) Date of Patent: Sep. 3, 2019

(54) METHOD FOR ARTIFICIAL CULTIVATION OF OPHIOCORDYCEPS SINENSIS FRUITING BODIES

(71) Applicant: GUANGDONG ENTOMOLOGICAL INSTITUTE, Guangzhou, Guangdong (CN)

(72) Inventors: Li Cao, Guangzhou (CN); Richou Han, Guangzhou (CN)

(73) Assignee: GUANGDONG INSTITUTE OF APPLIED BIOLOGICAL RESOURCES, Guangdon (CN)

( * ) Notice: Subject to any disclaimer, the term of this patent is extended or adjusted under 35 U.S.C. 154(b) by 241 days.

(21) Appl. No.: 15/122,763

(22) PCT Filed: Dec. 2, 2014

(86) PCT No.: PCT/CN2014/092747
§ 371 (c)(1),
(2) Date: Aug. 31, 2016

(87) PCT Pub. No.: WO2015/196734
PCT Pub. Date: Dec. 30, 2015

(65) Prior Publication Data
US 2017/0067011 A1    Mar. 9, 2017

(30) Foreign Application Priority Data
Jun. 25, 2014  (CN) .......................... 2014 1 0289703

(51) Int. Cl.
*A01G 18/00*    (2018.01)
*A01G 18/60*    (2018.01)
(Continued)

(52) U.S. Cl.
CPC ............... *C12N 1/14* (2013.01); *A01G 18/00* (2018.02); *A01G 18/60* (2018.02); *A01G 18/64* (2018.02); *C12R 1/645* (2013.01)

(58) Field of Classification Search
CPC ......... A01G 18/00; A01G 18/60; A01G 18/61
(Continued)

(56) References Cited

U.S. PATENT DOCUMENTS

2016/0345504 A1* 12/2016 Yang .................. A01G 18/00
2016/0345554 A1* 12/2016 Cao .................... A01K 67/033
2018/0200224 A1*  7/2018 Stamets .............. A61K 31/192

FOREIGN PATENT DOCUMENTS

CN    101773052 A    7/2010
CN    102138437 A    8/2011
(Continued)

OTHER PUBLICATIONS

International Search Report dated Feb. 15, 2015, issued in counterpart International Application No. PCT/CN2014/092747 (3 pages).

*Primary Examiner* — David J Parsley
(74) *Attorney, Agent, or Firm* — Westerman, Hattori, Daniels & Adrian, LLP

(57) ABSTRACT

A method for artificial cultivation of *Ophiocordyceps sinensis* fruiting bodies. The method comprises: inoculating *Ophiocordyceps sinensis* into a sterile rice medium, cultivating at 9-13° C. for 40-60 days, after the medium is covered with mycelia, performing low-temperature induction at 1-8° C. for 60-80 days to develop a fruiting body primordium, and transferring the cultivation to 11-16° C. till harvest of the fruiting bodies. The method requires no low-oxygen environment, which can reduce cultivation cost; it only needs 3-4 months from induction to harvest of fruiting bodies: the rice medium for use has a low cost, (Continued)

which is suitable for commercial cultivation of *Ophiocordyceps sinensis* fruiting bodies.

1 Claim, 1 Drawing Sheet

(51) Int. Cl.
 *C12N 1/14* (2006.01)
 *C12R 1/645* (2006.01)
 *A01G 18/64* (2018.01)
(58) Field of Classification Search
 USPC .............................................. 47/1.1, 58.1 R
 See application file for complete search history.

(56) References Cited

FOREIGN PATENT DOCUMENTS

| | | |
|---|---|---|
| CN | 102187786 A | 9/2011 |
| CN | 102613007 A | 8/2012 |
| CN | 103650910 A | 3/2014 |
| CN | 104082034 A | 10/2014 |

\* cited by examiner

METHOD FOR ARTIFICIAL CULTIVATION OF OPHIOCORDYCEPS SINENSIS FRUITING BODIES

FIELD OF THE INVENTION

The present invention belongs to the field of microorganism technology particularly relates to a method for artificial cultivation of *Ophiocordyceps sinensis* fruiting bodies.

BACKGROUND OF THE INVENTION

*Ophiocordyceps sinensis* (synonym: *Cordyceps sinensis*) is the most unique biological resource in China, belongs to Ascomycota, Sordariomycetes, Hypocreales, Ophiocordycipitaceae, *Ophiocordyceps*, and mainly originates in Tibet Qinghai, Yunnan, Sichuan, Gansu and other snow-capped and cold highland areas with an altitude over 3,000 meters in China. *Ophiocordyceps sinensis* fungus infects host insect, i.e., ghost moth larva and inactivates it, and the fungus-infected inactivated insect grows under a suitable condition to form an insect (inactivated insect) and grass (fungal fruiting body) composite morphological structure which is the authentic medicinal *Ophiocordyceps sinensis*.

Medicinal and edible *Ophiocordyceps sinensis* is excellent in a plurality of functions, such as tonifying liver and kidney benefiting vital energy, regulating various consumptive diseases. In modern medicine, *Ophiocordyceps sinensis* is regarded as a natural immune regulator, a "natural large combination therapy" for human health care. *Ophiocordyceps sinensis* may produce a variety of physiologically active substances with anti-bacterial, anti-viral, anti-tumor, anti-radiation and immune-regulating functions, and has a wide application in medicine, food and modern biotechnology, etc., especially plays an important role in traditional tonic market in China, always wins trust and favor from nationals, and realizes hot sell in Japan, Korea, Southeast Asia, the United States and other international markets. Depletion of resources, strong demands and protection policies lead to its soaring market price. Wild *Ophiocordyceps sinensis* has been listed as a species under national secondary protection. In order to protect Qinghai-Tibet Plateau ecology and A*Ophiocordyceps sinensis* resources so that *Ophiocordyceps sinensis* better serves human health, the only option is artificial Cultivation. However, due to harsh growing conditions if *Ophiocordyceps sinensis*, currently no mass artificial cultivation technology is available for *Ophiocordyceps sinensis*, although ferment cultivation of *Ophiocordyceps sinensis* anamorph-*Ophiocordyceps sinensis* or related fungi as well as products thereof have been put into market (Zhou et al., 2013, Informa Heathcare, DOI: 10.3109/07388551.791.245; Yue et al., 2013, International Journal of Medicinal Mushrooms, 15: 425-434.).

Currently few species of *Ophiocordyceps sinensis* fruiting bodies can be artificially cultivated successfully in the world. In addition to using a rice-containing medium to cultivate *Cordyceps minlitaris* fruiting bodies, *Cordyceps minlitaris* can be cultivated by using the insect as a host. Pan Zhonghua et al. (2002) (Jiangsu Sericulture, 24: 21-24) and Wang Xiqiang et al. (2002) (Journal of Anhui Agricultural Sciences, 30: 965-968) respectively use *Bombyx mori* L. and *Cryptotympaua pustulata* F. to cultivate *Cordyceps minlitaris*. Li Ruchun et al. (2005) (Mycosystema, 24: 349-355) infects *Tenebrio molitor* L. with *C. formosana* fungus to form rhizomorph. Li Taihui et al. (2005) (the national invention patent ZL200510101348.0) uses artificially cultivated *Tenebrio molitor* L. pupae to cultivate *Cordyceps minlitaris* stroma successfully. Some patents also describe methods for cultivation of *Cordyceps minlitaris* with silkworm pupae (Xu Daotian et al., 2000, ZL00130381.3; Li Jian, 2001, ZL01141386.7; Chen Ruiying et al., 1997, ZL97113190.2). Han Richou et al. (2006) (the national invention patent ZL200610123355.5) uses *Galleria mellonella* larvae to successfully cultivate *Cordyceps minlitaris* fruiting bodies.

Although in the invention patent application CN.201310432723.4, entitled "*Ophiocordyceps sinensis* fruiting body and cultivation method thereof", an *Ophiocordyceps sinensis* fruiting body can be cultivated, but the application has the following three defects: 1. it requires as low-oxygen concentration (10 to 15% oxygen concentration) from inducing a fruiting body to developing the fruiting body, and if in the region with low altitude, maintaining the low-oxygen concentration for 5-6 months requires quite a substantial cost; 2, it requires a long period up to 5-6 months from inducing a fruiting body to developing the fruiting body; 3, the medium costs much and is not suitable for mass commercial cultivation.

SUMMARY OF THE INVENTION

The objective of the present invention is to provide a method for commercially artificial cultivation of *Ophiocordyceps sinensis* fruiting bodies under normal oxygen concentrations in low altitude regions, which requires no low-oxygen environment.

The method for artificial cultivation of *Ophiocordyceps sinensis* fruiting bodies of the present invention comprising the following steps:

inoculating *Ophiocordyceps sinensis* into a sterile cultivation medium, cultivating at 9-13° C. for 40-60 days, after the medium is covered with mycelia, performing low-temperature induction at 1-8° C. for 60-80 days to develop a fruiting body primordium, transferring the cultivation to 11-16° C. for 30-40 days to harvest rod-like, unbranched taupe fruiting bodies with lengths ranging from 4 to 12 cm and similar morphology to the wildly collected *Ophiocordyceps sinensis* fruiting bodies.

The cultivation medium is formed by mixing rice with nutrient solution by a weight ratio of 1:1-1.5, the nutrient solution, by the total mass fraction of 100%, comprises glucose 2%, $KH_2PO_4$ 0.2%, $MgSO_4$ 0.1%, ammonium citrate 0.1%, peptone 0.5%, silkworm pupae powder 0.2%, and the balance of water, with the pH of 6.0-5.5.

Preferably in the step of inoculating *Ophiocordyceps sinensis* into a sterile cultivation medium, the *Ophiocordyceps sinensis* is prepared by the following method:

(1) preparation of parent species: inoculating *Ophiocordyceps sinensis* into a solid PPDA medium, cultivating at 9-16° C. for 45-60 days, and then selecting typical *Ophiocordyceps sinensis* colonies as the parent species; and (2) preparation of liquid strains: inoculating the colonies of parent species into a liquid PPDA medium, performing shaking cultivation at 9-16° C. for 40-60 days, selecting mycelial pellets with uniform size and diameter of 2-3 mm as the liquid strains;

in a sterile environment, diluting the liquid strains with sterile water 5-10 times, then inoculating them onto the sterile cultivation medium.

The solid PPDA medium of the present invention is a common medium used in the prior art, and it comprises glucose 20 g potato 200 g, peptone 10 g, $KH_2PO_4$ 3 g, $MgSO_4 \cdot 7H_2O$ 1.5 g, VB1 0.02 g, agar 15 g, and $H_2O$ 1000 mL in its formula, with natural pH. The preparation method thereof is: washing and peeling of potatoes, adding water and cooking the potatoes to rags, then filtering with gauze, adding glucose, peptone, $KH_2PO_4$, $MgSO_4 \cdot 7H_2O$, VB1, and agar to the filtrate, metering to a fixed volume of IL by using water, and sterilizing at 121° C. for 30 minutes for later use. The liquid PPDA medium refers to a medium with agar removed from the solid PPDA medium, prepared as the above method, but excluding agar.

The present invention can achieve the objective of the present invention through multiple repetitions, namely successfully scaling up cultivation of *Ophiocordyceps sinensis* fruiting bodies. Creating cultivation conditions for fruiting bodies is critical to the realization of the present invention.

*Ophiocordyceps sinensis* fruiting bodies derived from the cultivation method of the present invention have similar morphology to the wild *Ophiocordyceps sinensis* fruiting bodies, and contain main ingredients not lower than wild *Ophiocordyceps sinensis* in content, which can be applied as food. The following, is the analysis results of main ingredients in wild *Ophiocordyceps sinensis* fruiting bodies and *Ophiocordyceps sinensis* fruiting bodies derived from the artificial cultivation method of the present invention, specifically as shown in Table 1.

TABLE 1

Analysis results of main ingredients in *Ophiocordyceps sinensis* fruiting bodies artificially cultivated of the present invention and wild *Ophiocordyceps sinensis* fruiting bodies

| Analysis items | Artificially cultivated *Ophiocordyceps sinensis* fruiting bodies | Wild *Ophiocordyceps sinensis* fruiting bodies |
| --- | --- | --- |
| Polysaccharide (g/100 g fruiting bodies) | 3.37 | 1.07 |
| Ergosterol (mg/kg fruiting bodies) | 3500 | 813 |
| Cordycepic acid (g/100 g fruiting bodies) | 11 | 14 |

The method for artificial cultivation of *Ophiocordyceps sinensis* fruiting bodies in the present invention is performed under normal oxygen concentrations in low altitude regions, which does not require 10 to 15% low-oxygen concentration, thus significantly reducing cultivation cost; it only requires 90-120 days (i.e. 3-4 months) from inducing the fruiting bodies to harvesting fruiting bodies, shortening the cultivation time; the rice medium employed in the present invention has a low cost and is suitable for mass commercial cultivation of *Ophiocordyceps sinensis*.

BRIEF DESCRIPTION OF THE DRAWINGS

FIG. 1 is a view of *Ophiocordyceps sinensis* fruiting bodies cultivated in the present invention.

DETAILED DESCRIPTION OF THE EMBODIMENTS

The following examples further illustrate the present invention, rather than limiting the present invention.

Example 1

Experimental Location: Guangdong Entomological Institute Located in Guangzhou. The Following Cultivations are All Performed Under Conventional Oxygen Concentrations of Air.

Inoculating *Ophiocordyceps sinensis* into a sterile solid PPDA medium, performing dark cultivation at 9° C. for 60 days, and selecting typical *Ophiocordyceps sinensis* colonies as the parent species;

inoculating the colonies of parent species into a liquid PPDA medium, performing shaking cultivation at 9° C. and 100 rpm for 60 days, and selecting mycelial pellets with uniform size and diameter of 2-3 mm as the liquid strains for cultivation production of *Ophiocordyceps sinensis*.

In a sterile room or a clean bench, inoculating liquid strains, which are diluted 5 times by sterile water, into a sterile cultivation medium, placing the inoculated cultivation flask at 9° C. for 60 days, after the medium is covered with mycelia, performing low-temperature induction at 1° C. for 60 days for developing a fruiting body primordium, transferring the cultivation to 11° C. for 40 days to harvest fruiting bodies with lengths up to 4-8 cm, that is, it is 100 days from induction at a low temperature to developing fruiting bodies available for harvesting, wherein artificially cultivated *Ophiocordyceps sinensis* fruiting bodies are as shown in FIG. 1, and said *Ophiocordyceps sinensis* fruiting bodies have similar morphology to the wild *Ophiocordyceps sinensis* fruiting bodies, and contain main ingredients not lower than wild *Ophiocordyceps sinensis* in content, which can be applied as food.

The cultivation medium is prepared by the following method: dissolving glucose 20 g. $KH_2PO_4$ 2 g, $MgSO_4$ 1 g, ammonium citrate 1 g, peptone 5 g, and silkworm pupae powder 2 g in a small amount of water, with the pH value of 6.0-6.5, then metering to a fixed volume 1 L to obtain the nutrient solution, mixing rice with the nutrient solution by a weight ratio of 1:1, stirring the mixture, packing in cultivation flasks, and sterilizing at 121° C. for 60 minutes for later use.

Example 2

Experimental Location: Guangdong Entomological Institute Located in Guangzhou. The Following Cultivations are All Performed Under Conventional Oxygen Concentrations of Air.

Inoculating *Ophiocordyceps sinensis* into a sterile solid PPDA medium, performing dark cultivation at 16° C. for 45 days, and selecting typical *Ophiocordyceps sinensis* colonies as the parent species;

inoculating the colonies of parent species into a liquid PPDA medium, performing shaking cultivation at 16° C. and 100 rpm for 40 days, and selecting mycelial pellets with uniform size and diameter of 2-3 mm as the liquid strains for cultivation production of *Ophiocordyceps sinensis*.

In a sterile room or a clean bench, inoculating liquid strains, which are diluted 10 times by sterile water, into a sterile cultivation medium, placing the inoculated cultivation flask at 13° C. for 40 days, after the medium is covered with mycelia, performing low-temperature induction at 8° C. for 80 days for developing a fruiting body primordium, transferring the cultivation to 16° C. for 30 days to harvest fruiting bodies with lengths up to 4-6 cm, that is, it is 110 days from induction at a low temperature to developing fruiting bodies available for harvesting, wherein artificially cultivated *Ophiocordyceps sinensis* fruiting bodies are as shown in FIG. 1, and said *Ophiocordyceps sinensis* fruiting bodies have similar morphology to the wild *Ophiocordyceps sinensis* fruiting bodies, and contain main ingredients not lower than wild *Ophiocordyceps sinensis* in content, which can be applied as food.

The cultivation medium is prepared by the following method: dissolving glucose 20 g. $KH_2PO_4$ 2 g, $MgSO_4$ 1 g, ammonium citrate 1 g, peptone 5 g, and silkworm pupae powder 2 g in a small amount of water, with the pH value of 6.0-6.5 then metering to a fixed volume of 1 L to obtain the nutrient solution, mixing rice with the nutrient solution by a weight ratio of 1:1.5, stirring the mixture, packing in cultivation flasks, and sterilizing at 121° C. for 60 minutes for later use.

Example 3

Experimental Location: Guangdong Entomological Institute Located in Guangzhou. The Following Cultivations are All Performed Under Conventional Oxygen Concentrations of Air.

Inoculating *Ophiocordyceps sinensis* into a sterile solid PPDA medium, performing dark cultivation at 11° C. for 53 days, and selecting typical *Ophiocordyceps sinensis* colonies as the parent species;

inoculating the colonies of parent species into a liquid PPDA medium, performing shaking cultivation at 11° C. and 100 rpm for 50 days, and selecting mycelial pellets with uniform size and diameter of 2-3 mm as the liquid strains for cultivation production of *Ophiocordyceps sinensis*.

In a sterile room or a clean bench, inoculating liquid strains, which are diluted 7 times by sterile water, into a sterile cultivation medium, placing the inoculated cultivation flask at 11° C. for 50 clays until the medium is covered with mycelia, performing low-temperature induction at 5° C. for 65 days for developing a fruiting body primordium, transferring the cultivation to 13° C. for 35 days to harvest fruiting bodies with lengths up to 4-12 cm, that is, it is 100 days from induction at a low temperature to developing fruiting bodies available for harvesting, wherein artificially cultivated *Ophiocordyceps sinensis* fruiting bodies are as shown in FIG. 1, and said *Ophiocordyceps sinensis* fruiting bodies have similar morphology to the wild *Ophiocordyceps sinensis* fruiting bodies, and contain main ingredients not lower than wild *Ophiocordyceps sinensis* in content, which can be applied as food.

The cultivation medium is prepared by the following method: dissolving glucose 20 g. $KH_2PO_4$ 2 g, $MgSO_4$ 1 g, ammonium citrate 1 g, peptone 5 g, and silkworm pupae powder 2 g in a small amount of water, with the pH value of 6.0-6.5, then metering to a fixed volume of 1 L to obtain the nutrient solution, mixing rice with the nutrient solution by a weight ratio of 1:1.3, stirring the mixture, packing in cultivation flasks, and sterilizing for later use.

The invention claimed is:

1. A method for artificial cultivation of *Ophiocordyceps sinensis* fruiting bodies, comprising the following steps:
   inoculating *Ophiocordyceps sinensis* into a sterile cultivation medium, cultivating at 9-13° C. for 40-60 days, covering the sterile cultivation medium with mycelia and after the sterile cultivation medium is covered with mycelia, performing low-temperature induction at 1-8° C. for 60-80 days to develop a fruiting-body primordium, cultivating the fruiting-body primordium at 11-16° C. to harvest fruiting bodies;
   wherein the sterile cultivation medium is obtained by mixing rice with a nutrient solution by weight ratio of 1:1-1.5, and the nutrient solution, by a total mass fraction of 100%, comprises glucose 2%, KH2PO4 0.2%, MgSO4 0.1%, ammonium citrate 0.1%, peptone 0.5%, silkworm pupae powder 0.2%, and a balance of water, with a pH of 6.0-6.5,
   wherein the *Ophiocordyceps sinensis* is prepared by the following method:
   (1) preparing a parent species by inoculating *Ophiocordyceps sinensis* into a solid PPDA medium, performing dark cultivation at 9-16° C. for 45-60 days, and then selecting *Ophiocordyceps sinensis* colonies that have similar morphology to a wild *Ophiocordyceps sinensis* as the parent species;
   (2) preparing a liquid strains by inoculating the colonies of the parent species into a liquid PPDA medium, performing shaking cultivation at 9-16° C. for 40-60 days, selecting mycelial pellets with uniform size and diameter of 2-3 mm as the liquid strains;
   (3) in a sterile environment, diluting the liquid strains with sterile water 5-10 times, then inoculating them onto the sterile cultivation medium,
   wherein each liter of the solid PPDA medium comprises glucose 20 g, potato 200 g, peptone 10 g, KH2PO4 3 g, MgSO4.7H2O 1.5 g, VB1 0.02 g, agar 15 g, and a balance of water, with natural pH;
   wherein each liter of the liquid PPDA medium comprises glucose 20 g, potato 200 g, peptone 10 g, KH2PO4 3 g, MgSO4.7H2O 1.5 g, VB1 0.02 g, and a balance of water, with natural pH.

* * * * *